(12) United States Patent
Cope et al.

(10) Patent No.: US 12,097,170 B2
(45) Date of Patent: Sep. 24, 2024

(54) PACKAGED, SEALED CONTAINER SYSTEM FOR STABLE STORAGE OF AN OXYGEN SENSITIVE PHARMACEUTICAL FORMULATION

(71) Applicants: BAXTER INTERNATIONAL INC., Deerfield, IL (US); BAXTER HEALTHCARE SA, Glattpark (CH)

(72) Inventors: Steven M. Cope, Lake Villa, IL (US); Allan E. Titus, Deerfield, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 0 days.

(21) Appl. No.: 17/249,642

(22) Filed: Mar. 8, 2021

(65) Prior Publication Data
US 2021/0275470 A1    Sep. 9, 2021

Related U.S. Application Data

(60) Provisional application No. 62/986,606, filed on Mar. 6, 2020.

(51) Int. Cl.
*A61K 31/137* (2006.01)
*A61J 1/10* (2006.01)
(Continued)

(52) U.S. Cl.
CPC ............ *A61K 31/137* (2013.01); *A61J 1/10* (2013.01); *A61J 1/1468* (2015.05); *A61M 5/002* (2013.01);
(Continued)

(58) Field of Classification Search
CPC .... A61J 1/10; A61J 1/1468; A61J 1/14; A61J 1/1475; B65D 75/28; B65D 81/266; A61M 5/14
See application file for complete search history.

(56) References Cited

U.S. PATENT DOCUMENTS 5,849,843 A   12/1998  Laurin et al.
5,998,019 A   12/1999  Rosenbaum et al.
(Continued)

FOREIGN PATENT DOCUMENTS

CN   102525895 B   11/2013
EP    3124005 A1    2/2017
(Continued)

OTHER PUBLICATIONS

International Application No. PCT/US2021/021321, Invitation to Pay Additional Fees, mailed Jun. 22, 2021.
(Continued)

*Primary Examiner* — Jessica Arble
*Assistant Examiner* — Arjuna P Chatrathi
(74) *Attorney, Agent, or Firm* — Womble Bond Dickinson (US) LLP

(57) ABSTRACT

A packaged, sealed container system for stable storage of a formulation of an oxygen-sensitive pharmaceutical compound, the packaged, sealed container system comprising a primary container including therein a formulation of an oxygen-sensitive pharmaceutical compound, a secondary outer container comprising a first flexible sheet layer, an opposing second flexible sheet layer, and a seal disposed along a common peripheral edge of the first and second flexible sheet layers, such that the primary container is disposed between and enclosed by the first and second flexible sheet layers of the secondary outer container. An oxygen scavenger is also disposed between and enclosed by the first and second flexible sheet layers of the secondary outer container. The oxygen scavenger is in fluid communication with the contents of the primary container.

30 Claims, 12 Drawing Sheets

(51) Int. Cl.
  *A61J 1/14* (2023.01)
  *A61M 5/00* (2006.01)
  *A61M 5/14* (2006.01)
  *B65D 75/28* (2006.01)
  *B65D 81/26* (2006.01)
  *A61M 1/14* (2006.01)

(52) U.S. Cl.
  CPC ........... B65D 75/28 (2013.01); B65D 81/266 (2013.01); *A61J 1/14* (2013.01); *A61J 1/1475* (2013.01); *A61M 1/14* (2013.01); *A61M 5/14* (2013.01)

(56) References Cited

U.S. PATENT DOCUMENTS

| | | | |
|---|---|---|---|
| 6,613,036 B1* | 9/2003 | Farmer | A61J 1/10 604/408 |
| 10,226,436 B2 | 3/2019 | Puri et al. | |
| 10,888,534 B2 | 1/2021 | Dusci et al. | |
| 2001/0008686 A1* | 7/2001 | Inoue | B32B 27/306 264/171.27 |
| 2004/0000219 A1 | 1/2004 | McNulty | |
| 2004/0054012 A1 | 3/2004 | Dietlin et al. | |
| 2005/0070613 A1 | 3/2005 | Dinnequin | |
| 2006/0240204 A1 | 10/2006 | Ling et al. | |
| 2008/0249499 A1 | 10/2008 | Vancaillie et al. | |
| 2009/0044700 A1 | 2/2009 | Dietlin et al. | |
| 2010/0247936 A1* | 9/2010 | Chang | B32B 27/28 428/476.3 |
| 2010/0256590 A1* | 10/2010 | Babrowicz | B32B 27/306 604/408 |
| 2013/0123298 A1 | 5/2013 | Julia | |
| 2013/0327677 A1* | 12/2013 | McDorman | B32B 15/00 206/524.2 |
| 2014/0262883 A1* | 9/2014 | Devouassoux | B65D 75/36 206/364 |
| 2016/0058715 A1* | 3/2016 | Rakesh | A61K 9/08 206/364 |
| 2017/0049720 A1* | 2/2017 | Mitidieri | A61P 9/00 |
| 2018/0036310 A1* | 2/2018 | Kumar | A61K 31/519 |
| 2018/0214394 A1* | 8/2018 | Puri | A61K 47/183 |

FOREIGN PATENT DOCUMENTS

| | | |
|---|---|---|
| EP | 3110399 B1 | 1/2018 |
| FR | 2880807 A1 | 7/2006 |
| JP | 2006-217975 A | 8/2006 |
| WO | WO-2004/000219 A2 | 12/2003 |
| WO | WO-2016/013049 A1 | 1/2016 |

OTHER PUBLICATIONS

Alain Borgeat, Expert Declaration review of US 2005/0070613, 5 pp. (Apr. 21, 2020).
Bathochromic Shift, Wikipedia Entry, downloaded from the Internet at: <https://en.wikipedia.org/w/index.php?title=Bathochromic_shift&oldid=761195798> 2 pp. (last edited Jan. 21, 2017).
Boomsma et al., Optimal collection and storage conditions for catecholamine measurements in human plasma and urine, Clin. Chem., 39(12):2503-8 (1993).
Corona-Avendano et al., Study on the stability of noradrenaline and on the determination of its acidity constants, Spectrochim Acta A Mol Biomol Spectrosc., 61(13-14):3139-44 (2005).
"Levophed—norepinephrine bitartrate injection, solution, concentrate", Product Label, 8 pp., Hospira, Inc. (Oct. 2020).
"Noradrenaline (Norepinephrine) 1 mg/ml Concentrate for Solution for Infusion", Summary of Product Characteristics, Hospira UK Ltd., 11 pp., downloaded from the Internet at: <http://www.medicines.org.uk/emc/product/4115/smpc/print> (updated May 14, 2018).
"Norepinephrine Bitartrate Injection, USP", eCatalog Product Information 1 pp., Baxter Healthcare Corporation (Jul. 2019).
"Norepinephrine Bitartrate Injection, USP", Product Information Sheet, Baxter Healthcare Corporation, 6 pp. (Oct. 31, 2018).
Parry et al., Physical and chemical considerations in the in vitro calibration of microdialysis probes for biogenic amine neurotransmitters and metabolites, J. Neurosci. Methods, 32(3):175-83 (Jun. 1990). [abstract].
Rigamonti, "Study Report—Diluted Noradrenaline", Sinetetica SA Via Penate 5 Ch 6850 Mendrisio, 10 pp. (Apr. 28, 2020).
Rigamonti, "Study Report—Diluted Noradrenaline", Sinetetica SA Via Penate 5 Ch 6850 Mendrisio, 9 pp. (Nov. 13, 2015).
Walker et al., Stability of norepinephrine solutions in normal saline and 5% dextrose in water, Can. J. Hosp. Pharm., 63(2):113-8 (2010).
Williams et al., A comparison of drug substance predicted chemical stability with ICH compliant stability studies, Drug Dev. Ind. Pharm, 45(3):379-86 (2019).
International Application No. PCT/US2021/021321, International Search Report and Written Opinion, mailed Aug. 12, 2021.
"Antioxidant Excipients." Spectrum Chemical Mfg Corp (Aug. 1, 2023), http://www.spectrumchemical.com/chemical/antioxidant-excipients.
Peddicord et al., Stability of High-Concentration Dopamine Hydrochloride, Norepinephrine Bitartrate, Epinephrine Hydrochloride, and Nitroglycerin in 5% Dextrose Injection, 54 Am. J. Health-System Pharmacy 1417 (1997).
Tremblay et al., Stability of Norepinephrine Infusions Prepared in Dextrose and Normal Saline Solutions, 55 Can. J. Anesthesia 163 (2008).
Walker et al., Stability of Norepinephrine Solutions in Normal Saline and 5% Dextrose in Water, 63 Can. J. Hosp. Pharmacy 113 (2010).
"Levophed®—Norepinephrine Bitartrate Injection, USP, solution, concentrate", Product Label, 5 pp., Hospira, Inc. (Jun. 2007).

* cited by examiner

PACKAGED, SEALED CONTAINER SYSTEM FOR STABLE STORAGE OF AN OXYGEN SENSITIVE PHARMACEUTICAL FORMULATION

CROSS REFERENCE TO RELATED APPLICATION

This application claims the benefit under 35 U.S.C. § 119(e) of U.S. provisional patent application Ser. No. 62/986,606, filed Mar. 6, 2020, the entire disclosure of which is incorporated herein by reference.

FIELD OF THE DISCLOSURE

The disclosure relates generally to a packaged, sealed container system for stable storage of a formulation of an oxygen-sensitive pharmaceutical compound. More particularly, the disclosure relates to a packaged, sealed container system for stable storage of a ready-to-use, stable norepinephrine formulation.

BACKGROUND

Numerous pharmaceutical compounds are known to be sensitive to oxygen. Degradation of pharmaceutically active compounds by oxidation is particularly undesirable, as it leads to loss in activity of the active ingredient and potentially also to various degradation products, which can make the pharmaceutical composition including the same to be unmarketable and/or cause undesirable physiological effects.

Norepinephrine, also known as noradrenaline, is a hormone and a neurotransmitter and an example of a pharmaceutical compound that is known to be sensitive to oxygen.

Norepinephrine directly stimulates adrenergic receptors to cause vasoconstriction of the radial smooth muscle of arteries and veins, and an increase in myocardial contractility and heart rate. It is given intravenously as a vasopressor medication for patients with critical hypotension. It is also known as l-arterenol, levarterenol and l-norepinephrine.

Norepinephrine is a catecholamine with a structure similar to that of a catechol. A catecholamine is an organic compound containing a benzene with two hydroxyl side groups on carbons 1 and 2, and a side chain amine. Norepinephrine bitartrate monohydrate, a pharmaceutically accepted salt form of norepinephrine, has the following chemical structure:

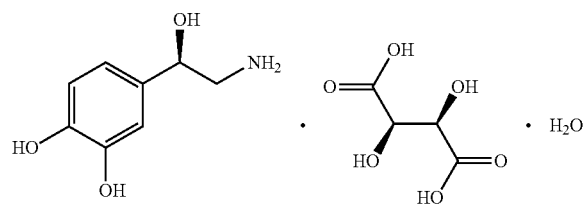 [SMILES: NC[C@H](O)c1ccc(O)c(O)c1 ; O=C(O)[C@H](O)[C@@H](O)C(=O)O ; O]

Norepinephrine has two stereoisomers, the R-isomer and the S-isomer. The norepinephrine bitartrate monohydrate salt shown above is a salt of the R-isomer and has the following IUPAC name: (−)-α-(aminomethyl)-3,4-dihydroxybenzyl alcohol tartrate monohydrate. The R-isomer is known to have a higher affinity to various receptors and is more potent than the S-isomer, which has negligible pharmaceutical activity. As a result, pharmaceutical compositions including substantially only the R-isomer of norepinephrine are typically administered to a patient, instead of a racemic mixture of the two isomers.

Norepinephrine is sparingly soluble in water, slightly soluble in alcohols and ethers, and readily soluble in acidic solutions. It is known to be light and oxygen sensitive, particularly in aqueous solutions. Degradation by oxidation is undesirable, as it leads to particulate formation and loss in activity of the active ingredient and also to various degradation products, namely noradrenalone and noradrenochrome, which cause undesirable physiological effects, and the latter of which renders the formulation a dark color, making the solution unmarketable.

Norepinephrine is administered by intravenous infusion for blood pressure control in certain acute hypotensive states (e.g. pheochromocytomectomy, sympathectomy, poliomyelitis, spinal anesthesia, myocardial infarction, septicemia, blood transfusion), as well as an adjunct in treatment of cardiac arrest and profound hypotension. It is commercially available, for example under the brand LEVOPHED® (Hospira, Inc.) in the United States, which uses sodium metabisulfite as an antioxidant in order to reduce degradation of norepinephrine by oxidation.

LEVOPHEDR's label warns that the antioxidant present in the formulation, sodium metabisulfite, may cause allergic-type reactions including anaphylactic symptoms and life-threatening or less severe asthmatic episodes in susceptible people. While the prevalence of sulfite sensitivity is unknown, it is seen more frequently in asthmatic than in nonasthmatic people. Due to the frequent use of norepinephrine in emergency situations, the risk and potential of further compromising a patient due to an allergic reaction to the antioxidant in the formulation is undesirable and disadvantageous. On the other hand, the oxygen sensitivity of the drug strongly suggests removing the antioxidant(s) from the formulation is problematic.

Furthermore, LEVOPHED® is not ready-to-use. Instead, it is generally sold in concentrated form, i.e. 4 mg/4 mL, that must be diluted immediately prior to administration to the patient. Typically, dilute and ready-to-use formulations of norepinephrine have poor long-term stability and generally expire twenty-four hours after dilution at room temperature. (See, e.g., Walker et al., Can. J. Hosp. Pharm, 63(2):113-8, 2010). Therefore, these commercial concentrates, containing norepinephrine and antioxidant, are diluted in various tonicity adjusted fluids in order to prepare a composition suitable for parenteral administration. The need for manual dilution introduces the risk of contamination due to routine handling and the risk of errors in calculations and dilutions, which can be disadvantageous for the patient.

SUMMARY OF THE INVENTION

In one aspect, a packaged, sealed container system for stable storage of a formulation of an oxygen-sensitive pharmaceutical compound is provided. The packaged, sealed container system includes a primary container including the oxygen-sensitive pharmaceutical formulation therein. The packaged, sealed container system further includes a secondary container. The secondary container comprises a first flexible sheet layer, an opposing second flexible sheet layer, and a seal disposed along a common peripheral edge of the first and second flexible sheet layers. The primary container is disposed between and enclosed by the first and second flexible sheet layers of the secondary container. The packaged, sealed container system further includes an oxygen scavenger disposed between and enclosed by the first and second flexible sheet layers of the secondary container.

In another aspect, a packaged, sealed container system for stable storage of a ready-to-use norepinephrine formulation is provided. The packaged, sealed container system includes a primary container including a ready-to-use norepinephrine formulation therein. The packaged, sealed container system further includes a secondary container. The secondary container comprises a first flexible sheet layer, an opposing second flexible sheet layer, and a seal disposed along a common peripheral edge of the first and second flexible sheet layers. The primary container is disposed between and enclosed by the first and second flexible sheet layers of the secondary container. The packaged, sealed container system further includes an oxygen scavenger disposed between and enclosed by the first and second flexible sheet layers of the secondary container. The ready-to-use norepinephrine formulation comprises about 0.01 to about 0.04 mg/ml norepinephrine and an aqueous tonicity adjusting agent, the ready-to-use norepinephrine formulation having a pH between about 3.4 and about 4.0, and the ready-to-use norepinephrine formulation being free of an antioxidant.

In a further aspect, a ready-to-use norepinephrine formulation comprising about 0.01 mg/ml to about 0.04 mg/ml norepinephrine, an aqueous tonicity adjusting agent, a pH between about 3.4 and about 4.0, wherein the formulation is free of an antioxidant is provided.

Further aspects of the disclosure may become apparent to those skilled in the art from a review of the following detailed description, taken in conjunction with the appended claims. While the invention is susceptible to embodiments in various forms, described herein are specific embodiments of the invention with the understanding that the disclosure is illustrative, and is not intended to limit the invention to specific embodiments described herein.

DETAILED DESCRIPTION

Figure 1:
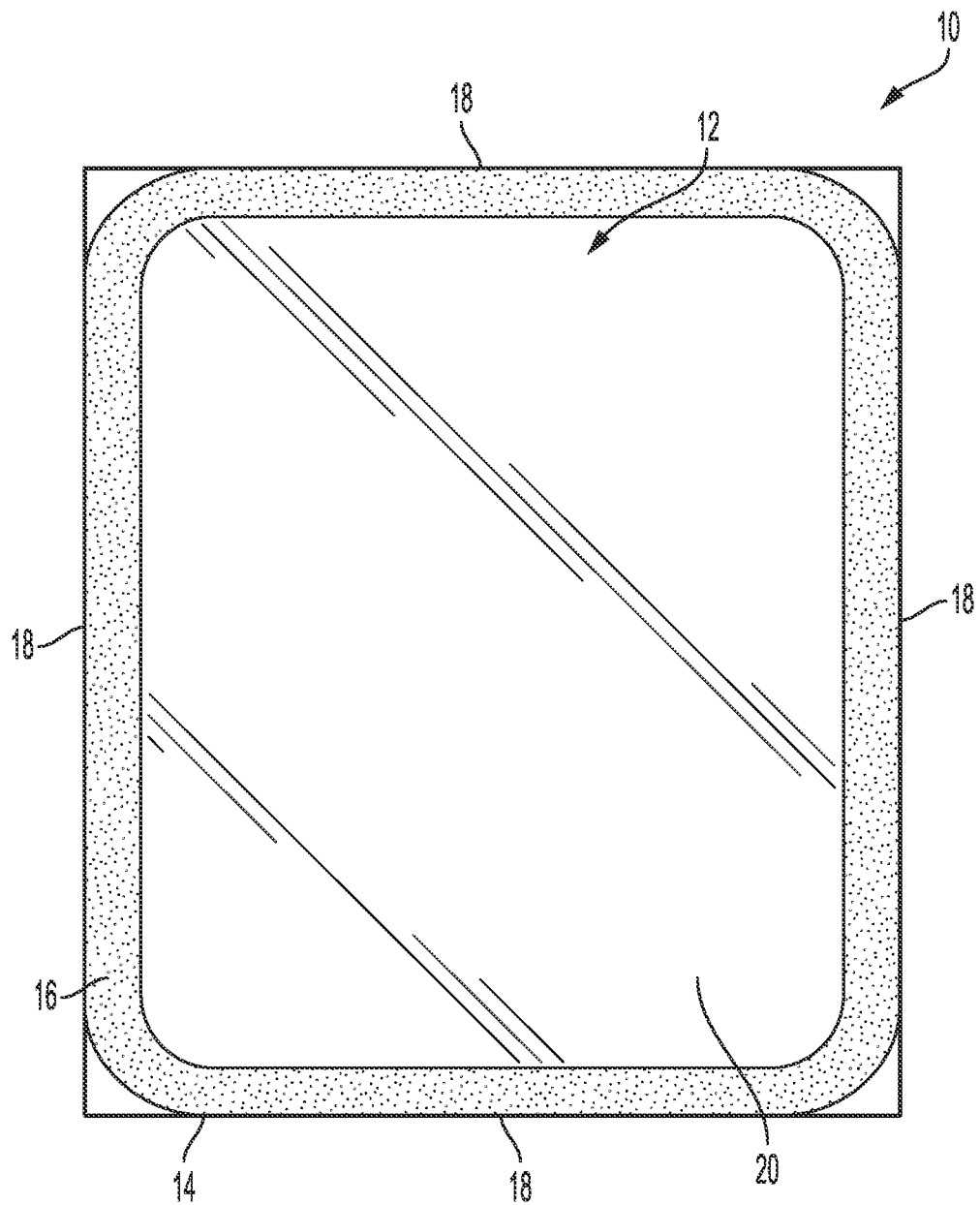
FIG. 1 is a plan view of an exemplary primary container according to the disclosure.

A packaged, sealed container system for stable storage of a formulation of an oxygen-sensitive pharmaceutical compound, the packaged, sealed container system comprising a primary container including therein a formulation of an oxygen-sensitive pharmaceutical compound is disclosed. The packaged, sealed container system further includes a secondary outer container comprising a first flexible sheet layer, an opposing second flexible sheet layer, and a seal disposed along a common peripheral edge of the first and second flexible sheet layers. The primary container is disposed between and enclosed by the first and second flexible sheet layers of the secondary outer container. An oxygen scavenger is also disposed between and enclosed by the first and second flexible sheet layers of the secondary outer container. As described in further detail herein, the packaged, sealed container system disclosed herein can advantageously facilitate and thereby significantly increase effective long-term, stable storage of the formulation of the oxygen-sensitive pharmaceutical compound contained therein.

Examples of oxygen-sensitive pharmaceutical compound formulations include formulations comprising norepinephrine, structurally similar catechol amines, and other pharmaceutically active compounds that are understood to be susceptible to oxygen degradation.

In one particular embodiment, the packaged, sealed container system facilitates long term storage of a ready-to-use norepinephrine formulation. The packaged, sealed container system includes a primary container including the ready-to-use norepinephrine formulation therein. The packaged, sealed container system further includes a secondary outer container comprising a first flexible sheet layer, an opposing second flexible sheet layer, and a seal disposed along a common peripheral edge of the first and second flexible sheet layers. The primary container is disposed between and enclosed by the first and second flexible sheet layers of the secondary outer container. An oxygen scavenger is also disposed between and enclosed by the secondary outer container. The ready-to-use norepinephrine formulation comprises about 0.01 to about 0.04 mg/ml norepinephrine, an aqueous tonicity adjusting agent, the ready-to-use norepinephrine formulation having a pH between 3.4 and 4.0, and the ready-to-use norepinephrine formulation is free of an antioxidant. As described in further detail herein, the packaged, sealed container system disclosed herein can advantageously facilitate and thereby significantly increase long-term, stable storage of the ready-to-use norepinephrine formulation.

In a further aspect, a ready-to-use norepinephrine formulation comprising about 0.01 mg/ml to about 0.04 mg/ml norepinephrine, an aqueous tonicity adjusting agent, a pH between about 3.4 and about 4.0, wherein the formulation is free of an antioxidant is provided.

Advantageously, the ready-to-use norepinephrine formulation demonstrates unexpected long-term stability at low norepinephrine concentrations even when the formulation is free of an antioxidant. As a result, the ready-to-use norepinephrine formulation does not need to undergo further additional dissolution procedures or dilution prior to administration to a patient, eliminating any risk of calculation or dilution error, as well as any contamination of the formulation from the same.

With respect to the long-term stability of the norepinephrine formulations disclosed herein, degradation is a much more significant concern for lower concentration ready-to-use norepinephrine formulations because oxidation of norepinephrine is a pseudo-zero order process that is independent of norepinephrine concentration and thus significantly more degradation occurs on a proportionate basis (particularly relative to concentrated formulations, for example, LEVOPHED®). In short, oxidative degradation of norepinephrine is a significant issue as it can lead to norepinephrine formulations with diminished potency, which can be particularly problematic at times of crisis when known dosage amounts are required to control critical hypotension in a patient. Thus, the long-term, stable storage of a ready-to-use norepinephrine formulation that is achieved with the packaged, sealed container system and norepinephrine formulations according to the disclosure affords both clinicians and patients with significant, practical benefits.

The term "ready-to-use," as used herein, means a formulation is sterile and suitable for immediate administration to the patient without the need for any additional dissolution procedures (such as solubilizing a lyophilized powder), dilutions, or other changes or additions to the formulation before administration.

The oxygen-sensitive pharmaceutical compound and ready-to-use norepinephrine formulations of the invention described herein are preferably stable compositions. As used herein, the term "stable" refers to a formulation that remains suitable for parenteral administration to a patient over a given period of time, typically over the shelf life of the product. Typically, the formulations are stable for at least 90 days, at least 120 days, at least 150 days, at least 180 days, and/or at least 1 year after storage at 5° C. or 25° C., e.g., the oxygen-sensitive pharmaceutical compound, e.g., norepinephrine, contained in the formulation retains at least about 90%, at least about 95%, and/or at least about 99% of the initial activity as measured by the initial and the final amounts of the oxygen-sensitive pharmaceutical compound, e.g., R-norepinephrine. The USP equates the shelf-life of a R-norepinephrine formulation to be the amount of time it takes for 10% of the product to degrade.

The term "norepinephrine," as used herein, includes norepinephrine free base and/or its pharmaceutically acceptable salts, such as norepinephrine bitartrate monohydrate. Norepinephrine is also known by other names such as noradrenaline, 1-arterenol, levarterenol and 1-norepinephrine. The norepinephrine, whether present in a given formulation as the free base of norepinephrine or a pharmaceutically acceptable salt thereof, comprises the R-isomer of norepinephrine. Typically, the ready-to-use, stable formulation of norepinephrine disclosed herein is free of the S-isomer of norepinephrine at the time the formulation is prepared and contains less than 10 wt. % of the S-isomer after terminal sterilization and storage of at least 90 days, at least 120 days, at least 150 days, at least 180 days, and/or at least 1 year at 5° C. or 25° C. Similarly, the term "oxygen-sensitive pharmaceutical compound," is understood include the corresponding free base and/or pharmaceutically acceptable salts thereof.

As used herein, "free of" means that the formulation of an oxygen-sensitive pharmaceutical compound such as the ready-to-use formulation of norepinephrine contains insignificant amounts of the indicated component. For example, the formulation of an oxygen-sensitive pharmaceutical compound such as the ready-to-use formulation of norepinephrine may contain less than 2.5 wt %, less than 2 wt %, less than 1.5 wt %, less than 1 wt %, less than 0.5 wt %, less than 0.1 wt %, more preferably less than 0.05 wt %, based on the weight of the composition, of the S-isomer of norepinephrine (or other indicated component) at the time the formulation is prepared. Additionally, the formulation of an oxygen-sensitive pharmaceutical compound, e.g., the ready-to-use formulation of norepinephrine may contain less than 2.5 wt %, less than 2 wt %, less than 1.5 wt %, less than 1 wt %, less than 0.5 wt %, less than 0.1 wt %, more preferably less than 0.05 wt %, based on the weight of the formulation, of an antioxidant. The term "antioxidant," as used herein, refers to any antioxidant that can be typically be used in a parenteral formulation, but is not included in significant amounts in the ready-to-use norepinephrine formulations described herein. Specific antioxidants that may be excluded from the ready-to-use norepinephrine formulations described herein include sodium sulfite, sodium bisulfite, sodium metabisulfite, ascorbic acid, cysteine, as well as other antioxidants for parenteral formulations, and combinations thereof. In particular, it has been found that ascorbic acid should be avoided.

As used herein, the term "about" means+/−10% of any recited value, or in an alternative embodiment, +/−5% of any recited value. As used herein, this term modifies any recited value, range of values, or endpoints of one or more ranges.

The term "therapeutically effective amount," as used herein, refers to an amount of a pharmaceutical formulation comprising an oxygen-sensitive pharmaceutical compound, for example, norepinephrine, or a pharmaceutically acceptable salt thereof, which is sufficient to treat or mitigate a condition, for example, to control blood pressure of an individual in acute hypotensive states, such as pheochromocytomectomy, sympathectomy, poliomyelitis, spinal anesthesia, myocardial infarction, septicemia, blood transfusion and/or drug reactions.

In another aspect, the term "therapeutically effective amount," as used herein, refers to an amount of a pharmaceutical formulation comprising an oxygen-sensitive pharmaceutical compound, for example, norepinephrine, which is sufficient to serve as an adjunct in treating a condition, for example, cardiac arrest and/or profound hypotension.

The term "pharmaceutically acceptable salt," as used herein, refers to those salts which retain the biological efficacy and properties of the corresponding oxygen-sensitive pharmaceutical compound, for example, norepinephrine, and which are not biologically or otherwise undesirable. Such salts can be formed with inorganic acids such as hydrochloric acid, hydrobromic acid, sulfuric acid, nitric acid, phosphoric acid, and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. In embodiments, the pharmaceutically acceptable salt of norepinephrine is (R)-α-(aminomethyl)-3,4-dihydroxybenzyl alcohol tartrate monohydrate, hereinafter referred to as "norepinephrine bitartrate monohydrate."

The term "hypotension," as used herein, refers to abnormally low blood pressure. As appreciated by those of skill in the art, blood pressure characterized as "hypotensive" may vary from individual to individual. Hypotension, however, is generally defined as systolic pressure less than 90 mmHg and/or diastolic pressure less than 50 mmHg.

The term "parenteral administration," as used herein, refers to the administration or infusion of a drug and/or drug formulation to a subject elsewhere in the body than the mouth. Suitable routes for parenteral administration include intravenous, subcutaneous, intradermal, intramuscular, intraarticular, and intrathecal. In particular, the ready-to-use norepinephrine formulations described herein preferably are administered by intravenous infusion.

The ready-to-use norepinephrine formulation of the invention comprises a concentration of norepinephrine and an aqueous tonicity adjusting agent, wherein the formulation has a pH between about 3.4 and about 4.0 and is free of an antioxidant. In embodiments, the norepinephrine is in the form of norepinephrine bitartrate monohydrate.

The pharmaceutical formulations comprising an oxygen-sensitive pharmaceutical compound, for example, the ready-to-use norepinephrine formulations disclosed herein, may be packaged in any suitable primary container known in the art including but not limited to vials, syringes, bags, bottles and ampules presentations. Containers may be fabricated from glass or from polymeric materials.

The size of the primary container typically ranges from 1 ml to 500 ml. The formulations comprising an oxygen-sensitive pharmaceutical compound, for example, the ready-to-use norepinephrine formulations disclosed herein, may be filled into bags, bottles, ampules, or vials with sizes generally between 1 ml and 500 ml, for example, 50 mL or 100 mL bags. In addition, pre-filled syringes can be used as the primary container.

Suitable primary containers include flexible bags as disclosed in US 2008/0249499, which is hereby incorporated by reference in its entirety. The flexible bag, commonly referred to as an IV bag, may be formed by any of a number of methods, for example, by an exemplary form/fill/seal process where a sheet layer (or film) is aligned and then folded by a folding triangle. After that aligning and folding step, the film can be cut to allow the introduction of a port system (described below) between the two resulting facing films. The port system can then be automatically fed in place and welded between the two opposing faces of the folded film. By vertical welding the bottom part of the bag is formed and a hanger hole is punched. The side of the bag is formed by horizontal welding, while the solution for infusion is fed into the formed flexible bag. The upper horizontal welding also can form the lower side of the next bag. Finally, each bag is separated from the other during a sealing/cutting process. Thus, the flexible bag may be formed of a single sheet layer of flexible material, folded and sealed along the peripheral edges.

In other methods, two flexible sheets are joined at a top end and two side edges, i.e., when the two flexible sheets are placed in facing relationship they can be joined at their overlying/overlapping peripheral edges, while leaving an opening at a bottom end. The sealed top end and side edges, along with the open bottom end, are collectively referred to herein as the peripheral edges of the flexible bag. The top end includes a hanger aperture, which is preferably laterally offset from a central vertical axis of the flexible bag portion. The port system can then be fed in place and welded between the two opposing flexible sheets. Any other known method of bag manufacture, such as blow molding or vacuum forming, may also be used.

In one embodiment, a multilayer flexible sheet layer (or film) is used to manufacture the primary container. In one aspect according to this embodiment, the multilayer flexible sheet layer comprises a low density polyethylene (PE) bottom (inside facing when assembled) layer such as Stamylex 1026F, a polypropylene (PP) top (outside facing when assembled) layer such as Bormed RD804CF or Bormed RE816CF, and a polyamide (PA) middle layer such as Grilon FG40NL Natural 6021. A composite PE bottom layer may also be used. A composite PP top layer may also be used. Adhesion between the PP and PA layers may be achieved by a tie layer comprising PP grafted with maleic anhydride such as Admer QF300E. Similarly, adhesion between the PA and PE layers may be achieved by a tie layer comprising PE grafted with maleic anhydride such as Yparex 8104E.

The flexible sheet layer may have any suitable thickness, for example, between about 100 μm and about 250 μm, between about 125 μm and about 225 μm, and/or between about 150 μm and about 200 μm.

Such flexible bags necessarily include an administration port. In one embodiment, the primary container is a flexible bag with a single port adapted for fluid delivery (internally or externally), the single port comprising an administration port for delivering formulations comprising an oxygen-sensitive pharmaceutical compound, for example, the ready-to-use norepinephrine formulations disclosed herein, to a patient via connection to an administration set. Because the primary container includes a ready-to-use formulation therein, the primary container according to this embodiment does not include a separate functioning "injection" or "reconstitution" port that allows a fluid to be added to the formulation of the primary container. Instead, the primary container may include a non-accessible "dummy" port that does not include a frangible cannula or pierceable diaphragm or membrane and thus does not readily allow for communication between an interior of the primary container and the exterior. A "dummy" port is not considered to be a port as conventionally understood as it does not function provide access to the contents of the primary container. The dummy port may be substantially solid. As a result, the dummy port may be configured to prevent at least 90% of attempts to insert a standard 21 gauge needle at an insertion rate of 200 mm/min into the interior of the primary container using an insertion force of 5N or less, or even 10 N or less.

The port structure is preferably sized and configured to fit within the opening (not illustrated) in the bottom end of the bag. In a preferred embodiment, the opening and port structure are substantially as wide as the top edge, such that the port structure essentially defines the entire bottom surface of the bag. The port structure is formed of a plastic material that in the preferred embodiment is less flexible than the bag portion and is preferably molded as a single, integral unit. In this respect, the preferred port structure may be considered as having intermediate rigidity, as it is preferably more rigid than the generally flexible bag, but less than completely rigid such as glass or metal. The port structure typically includes a single functioning port as mentioned above.

In one embodiment, the port structure is molded from PE. The molded port system includes a non-accessible (dummy) port, which prevents addition of medication or diluent, and an administration port, which allows access to the bag contents as described above. The administration port may have a twist-off protective cap and a membrane in addition to a flexible sleeve. The twist off protector and the membrane may comprise PE. The flexible sleeve typically provides a non-dripless access connector (non-DAC) port configuration and in one embodiment may comprise a coextruded inner layer and outer layer. In one aspect, the inner layer may comprise a blend of polyurethane and silicone, such as TPSiV 3111-70A, and the outer layer may comprise an ethylene-vinyl acetate copolymer such as Ateva 1807 EG. The port system may be gamma irradiated prior to incorporation into the flexible bag structure.

Other flexible bags may be used. Preferred flexible bag primary containers may be free of PVC, such as those disclosed in U.S. Pat. Nos. 5,849,843 and 5,998,019, which are hereby incorporated by reference in their entirety. Suitable flexible polymeric primary containers include but are not limited to GALAXY IV containers (Baxter International Inc.), VIAFLO containers (Baxter International Inc.), and INTRAVIA containers (Baxter International Inc.).

The primary container is disposed within and enclosed by a secondary container. The secondary container may be an overpouch container. Overpouches are flexible containers that can be used as secondary containers in the packaged, sealed container systems disclosed herein to store, protect, and transport the primary containers containing a formulation comprising an oxygen-sensitive pharmaceutical compound such as norepinephrine therein. Generally, overpouches are provided by a first flexible sheet layer, an opposing second flexible sheet layer, and a seal disposed along a common peripheral edge of the first and second flexible sheet layers. Preferably, the secondary overpouch container should be optically transparent to enable visual inspection of the primary container and any other contents within the overpouch. It is also desirable for the overpouch container to be capable of withstanding autoclaving or other terminal sterilization process without causing the medical component therein to shrink/wrinkle and without becoming discolored and/or adhered to the medical component.

The overpouch container may be an aluminum overpouch, a light absorbing polymeric overpouch, or a similar barrier structure. In one embodiment, the primary container is in fluid communication with any other contents of the overpouch secondary container.

In one embodiment, the overpouch secondary container comprises a first flexible sheet layer comprising an amber transparent film and a second flexible sheet layer comprising an opaque aluminum laminated foil. The first flexible sheet layer of may be an amber transparent multilayer film comprising a PET (Polyethylene terephthalate)/PA/PP laminate to allow the contents within the secondary container, for example, any labeling on the primary container to be seen. The second flexible sheet layer may be an opaque laminated foil comprising a PET/PA/Aluminum foil/PP laminate. A seal is disposed along a common peripheral edge of the first and second flexible sheets.

In another embodiment, the overpouch secondary container comprises a first flexible single layer sheet layer comprising a polymeric blend of a high density polyethylene and a surface enhancing polymer, an opposing second flexible single layer sheet layer comprising a polymeric blend of a high density polyethylene and a surface enhancing polymer of an ethylene propylene diene terpolymer dispersed in a polyolefin matrix, and a seal disposed along a common peripheral edge of the first and second flexible sheets as disclosed in US 2006/0240204, which is hereby incorporated by reference in its entirety.

An oxygen scavenger is also disposed within and enclosed by the overpouch secondary container. A sachet located adjacent to the primary container and disposed within the secondary overpouch container may include the oxygen scavenger. The sachet (i.e., the bag) itself is porous and may comprise polyethylene materials. The oxygen scavenger may comprise iron powder, iron oxide powder, or a mixture thereof, for example, micronized iron. Other known oxygen scavengers may also be used. The oxygen scavenger is primarily included to absorb small amounts of oxygen that permeate through the secondary container during the shelf life of the drug product. Thus, despite the primary and secondary containers being sealed, the fluid contents of the primary container may be considered to be in fluid communication with the contents of the secondary container, including the oxygen scavenger. Thus, the oxygen scavenger can be considered to be in fluid communication with the formulation of the primary container.

When formulations of an oxygen-sensitive pharmaceutical, for example, ready-to-use norepinephrine formulations, are provided in a packaged, sealed container system as described herein, the formulations described herein are preferably stable compositions as described above, i.e., the formulations are stable for at least 90 days, at least 120 days, at least 150 days, at least 180 days, and/or at least 1 year at 5° C. or 25° C., such that, for example, the norepinephrine contained in the formulation retains at least about 90%, at least about 95%, and/or at least about 99% of the initial activity as measured by the initial and the final amounts of R-norepinephrine.

Advantageously, the ready-to-use norepinephrine formulation maintains long-term stability at low concentrations of norepinephrine while being substantially free of an antioxidant, particularly when packaged and sealed in the packaged, sealed container system described herein. As norepinephrine is generally understood in the art to be oxygen-sensitive, it was unexpected that the norepinephrine formulations according to the disclosure, particularly because of the very low concentrations of norepinephrine suitable for direct parenteral administration to a patient, shows substantially equivalent, or even improved, stability as compared to those formulations containing antioxidants such as cysteine, ascorbic acid, and sodium metabisulfite.

As used herein, the concentration of norepinephrine is generally defined in milligrams per milliliter (mg/ml), or mg/L, wherein each milligram is calculated based on the weight of the free base of norepinephrine. For example, if the salt norepinephrine bitartrate monohydrate (MW=337.28) is used in the formulation at 0.02 mg/ml, then there is about 0.01 mg/ml of norepinephrine free base (MW 169.18) in the formulation, or more specifically, about 0.01 mg/ml of norepinephrine as that term is used herein (as the bitartrate). In embodiments, the concentration of norepinephrine free base in the formulation according to the invention is between about 0.01 mg/ml and about 0.04 mg/ml, between about 0.015 mg/ml and about 0.035 mg/ml, and/or between about 0.02 mg/ml and about 0.03 mg/ml, for example, about 0.016 mg/ml, about 0.02 mg/ml, about 0.03 mg/ml, about 0.032 mg/ml, about 0.035 mg/ml, and less than 0.04 mg/ml. Each of these concentrations is suitable for direct administration to a patient. Such ready-to-use concentrations are clinically significant inasmuch as overdosage of norepinephrine can result in violent headache, photophobia, stabbing retrosternal pain, pallor, intense sweating, vomiting, severe hypertension, reflex bradycardia, marked increase in peripheral resistance, and decreased cardiac output.

In addition to the oxygen-sensitive pharmaceutical compound, for example, norepinephrine, the formulations according to the disclosure may further include other pharmaceutically acceptable additives, including tonicity adjusting agents, chelating agents, pH adjusting agents, and/or buffers.

The formulations of an oxygen-sensitive pharmaceutical compound, for example, ready-to-use norepinephrine formulations of the invention typically comprises an aqueous tonicity adjusting agent. The aqueous tonicity agent is added to adjust the osmolality of the aqueous solution and to reduce local irritation by preventing osmotic shock at the site of drug administration. The tonicity agent can be selected from, but not limited to sodium chloride, potassium chloride, calcium chloride, mannitol, glycerol, sorbitol, propylene glycol, dextrose, sucrose, and the like and mixtures thereof. In preferred embodiments, the aqueous tonicity adjusting agent of the invention is dextrose. In other preferred embodiments, the aqueous tonicity adjusting agent is sodium chloride. According to the prescribing information for LEVOPHED®, administration of norepinephrine formulations using a saline solution alone should expressly be avoided because oxidation reportedly occurs in saline solution alone such that a significant loss of potency is observed. Surprisingly, the ready-to-use norepinephrine formulation of the invention can maintain its stability and potency when sodium chloride alone is used as the aqueous tonicity agent.

One or more chelating agents may also be added to the formulations of an oxygen-sensitive pharmaceutical compound, for example, ready-to-use norepinephrine formulations according to the disclosure. Suitable chelating agents include disodium edetate dihydrate, disodium edetate, edetic acid, ethylenediamine tetraacetic acid, diethylenetriamine pentaacetic acid, and the like and mixtures thereof.

The ready-to-use norepinephrine formulation of the invention has a pH between about 3.4 and about 4.0. The long-term stability of the formulation is best when the pH is within this range. As demonstrated in Example 1, at relatively low PH levels, i.e. pH levels below 3.4, particularly below 3.0, the conversion of norepinephrine from the active R-isomer to the inactive S-isomer is significantly increased, rendering the formulation less potent and less effective. Additionally, at relatively high pH levels, i.e. PH levels above 4.0, particularly above 4.2, norepinephrine is more susceptible to degradation via oxidation to various degradation products. Therefore, a pH range of about 3.4 to about 4.0, about 3.5 to about 3.9, and/or about 3.6 to about 3.8 is desired. In preferred embodiments, the pH of the formulation is about 3.7.

The pH of the formulations according to the disclosure may be adjusted using a variety of pH adjusting agents to achieve these ranges. The pH adjusting agents of the invention may be selected from, but not limited to hydrochloric acid, sodium hydroxide, citric acid, sulfuric acid, acetic acid, tartaric acid, tromethamine, potassium hydroxide, and the like and mixtures thereof. In one preferred embodiment, the pH is adjusted with a mixture of hydrochloric acid and sodium hydroxide.

The ready-to-use norepinephrine formulation of the invention is free of and thus does not contain or include any significant amount of an antioxidant, i.e., an antioxidant is not added to the norepinephrine formulations. In fact, the inventors found that when the antioxidant ascorbic acid was included, the rate of degradation of norepinephrine actually increased relative to a formulation that did not contain an antioxidant. Therefore, the formulation of the invention demonstrates unexpected stability at least relative to a norepinephrine formulation containing ascorbic acid as an antioxidant. Furthermore, as shown in Example 1, the inventors found that the norepinephrine formulations without an antioxidant according to the disclosure surprisingly demonstrated improved long-term stability over a range of pH levels relative to comparable formulations containing cysteine as the antioxidant. Therefore, the norepinephrine formulations of the disclosure can demonstrate unexpected stability at least relative to a norepinephrine formulation containing cysteine as an antioxidant. As shown in Example 2, the norepinephrine formulations of the disclosure showed equal stability and performed at least as well as the formulation comprising sodium metabisulfite as an antioxidant. FIGS. 6 through 10 display various stability data of the formulation of the invention as compared to a formulation comprising sodium metabisulfite. Surprisingly, as seen in these figures, the stability of the formulation of the invention at room temperature for at least 90 days is comparable to that of the formulation with the antioxidant that is generally preferred in the LEVOPHED® state-of-the-art formulations.

Figure 11:
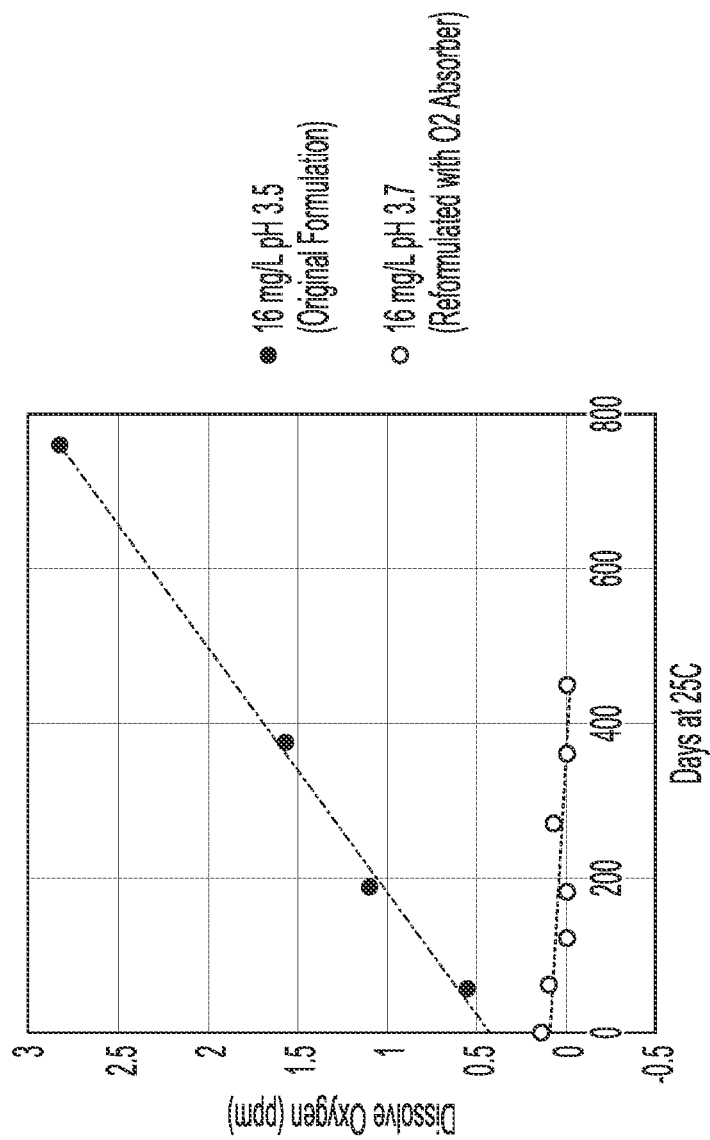
FIG. 11 is a graph illustrating the change in dissolved oxygen of norepinephrine formulations according to the disclosure when packaged in a primary container and disposed within a secondary container with or without an oxygen scavenger over time.

In preferred embodiments, the ready-to-use norepinephrine formulation is prepared under inert atmosphere, such as $N_2$ gas, so as to minimize and/or eliminate the presence of oxygen in the formulation. As best illustrated in FIG. 11, when packaged and sealed in the packaged, sealed container system described herein, the ready-to-use norepinephrine formulation advantageously has a dissolved oxygen level of less than 1 ppm, preferably less than 0.5 ppm, and more preferably less than 0.1 ppm (e.g., 0 ppm) after storage at 5° C. or 25° C. for 10 days, for 30 days, for 40 days, for 60 days, for 90 days, for 150 days, for 180 days, and/or at least 1 year, indicative of the long-term stability of the formulation.

The ready-to-use norepinephrine formulation suitable for parenteral administration disclosed herein is a preferably sterile composition. As used herein, the term "sterile" refers to a composition that has been brought to a state of sterility and has not been subsequently exposed to microbiological contamination, e.g., the primary container holding the sterile composition does not contain replicating microorganisms and has not been compromised such that it has been exposed to ambient atmosphere and/or biological contaminants. In pharmaceutical practice, a state of sterility exists when the probability is less than one out of one million that the composition is contaminated with replicating microorganisms. Sterile compositions in accordance with the invention are generally prepared in accordance with current Good Manufacturing Practice ("CGMP") regulations of the U.S. Food and Drug Administration.

Procedures for filling the norepinephrine formulation according to the invention in primary containers, and their subsequent processing are known in the art. Such procedures are well known and are often used to produce sterile pharmaceutical injectable drug products. Terminal sterilization, e.g., autoclaving, is conventionally used for sterilizing the formulation according to the invention.

In one embodiment, batches of the norepinephrine formulation according to the disclosure were prepared by introducing water into a clean and calibrated stainless steel tank to approximately 90% final batch volume; a tonicity agent such as dextrose was then added and mixed in until visually dissolved; nitrogen sparging of the solution was initiated and continued throughout mix and fill; when dissolved oxygen value was measured to be about 1 ppm, norepinephrine bitartrate monohydrate was added and mixed until visually dissolved; pH was adjusted to the desired target value between 3.4 and 4.0, for example, 3.7, with 1N hydrochloric acid; additional water was added to bring the batch to final batch volume; the formulation was flushed through a filter, such as a Millipore CVGL71TP3, 0.22 μm PVDF cartridge, and introduced into a separate hold vessel in which nitrogen sparging was continued; fill volume (~265 mL) was verified and the formulation was filled into previously nitrogen flushed and evacuated VIAFLO primary containers through the administration port; approximately 20 mL of nitrogen was injected, through the port, into the primary container head space (oxygen content: <1.5%); the primary container was sealed; and the sealed, filled primary container was placed inside an aluminum/amber overpouch, while nitrogen flushing/evacuating of the secondary container head space (oxygen content: <1.0% in ≤105 mL head space). The packaged, sealed system may then be autoclaved.

Sterile pharmaceutical formulations according to the present invention may also be prepared using aseptic processing techniques. Aseptic filling is ordinarily used to prepare drug products that will not withstand heat sterilization, but in which all of the ingredients are sterile. Sterility is maintained by using sterile materials and a controlled working environment. All containers and apparatus are sterilized, preferably by heat sterilization or by being exposed to a peroxide bath, prior to filling. The primary container (e.g., vial, ampule, bag, bottle, or syringe) is then filled under aseptic conditions. The primary container is then placed in a secondary container under aseptic conditions. Sterilization can be conducted by, for example, by filtration through a bacteria retaining filter, by incorporating sterilizing agents into the compositions, and using other known techniques.

The containers including the norepinephrine formulation as disclosed herein may be stored at any suitable temperature, for example, at room temperature or at a low temperature, for example, at a temperature between about −25° C. and about 50° C. Lower temperatures, particularly below freezing, may be preferred for long term storage.

The disclosure also provides a method of treating hypotension in a subject comprising administering to the subject a therapeutically effective amount of the ready-to-use norepinephrine formulations described herein, wherein the norepinephrine formulation comprises about 0.01 mg/ml to less than 0.04 mg/ml norepinephrine, an aqueous tonicity adjusting agent, a pH between about 3.4 and about 4.0, and is free of an antioxidant, and the subject is in need of treatment for hypotension.

Subjects in need of blood pressure control may be suffering from conditions that cause acute hypotension, such as pheochromocytomectomy, sympathectomy, poliomyelitis, spinal anesthesia, myocardial infarction, septicemia, blood transfusion and drug reactions. Subjects suffering from cardiac arrest and profound hypotension may also be treated with a formulation of the invention as an adjunct pharmaceutical to treat the associated hypotension. Typically, the norepinephrine formulation according to the disclosure is parenterally administered to the subject. In preferred embodiments, the ready-to-use formulation is administered by intravenous infusion.

FIG. 1 illustrates a suitable secondary container 10 in accordance with the disclosure. As illustrated, the secondary container is an overpouch comprising a first flexible sheet layer 12, an opposing second flexible sheet layer 14, and a seal 16 disposed along a common peripheral edge 18 of the first and second flexible sheet layers 12, 14 to define an inner chamber 20 of the container 10.

Figure 2A:
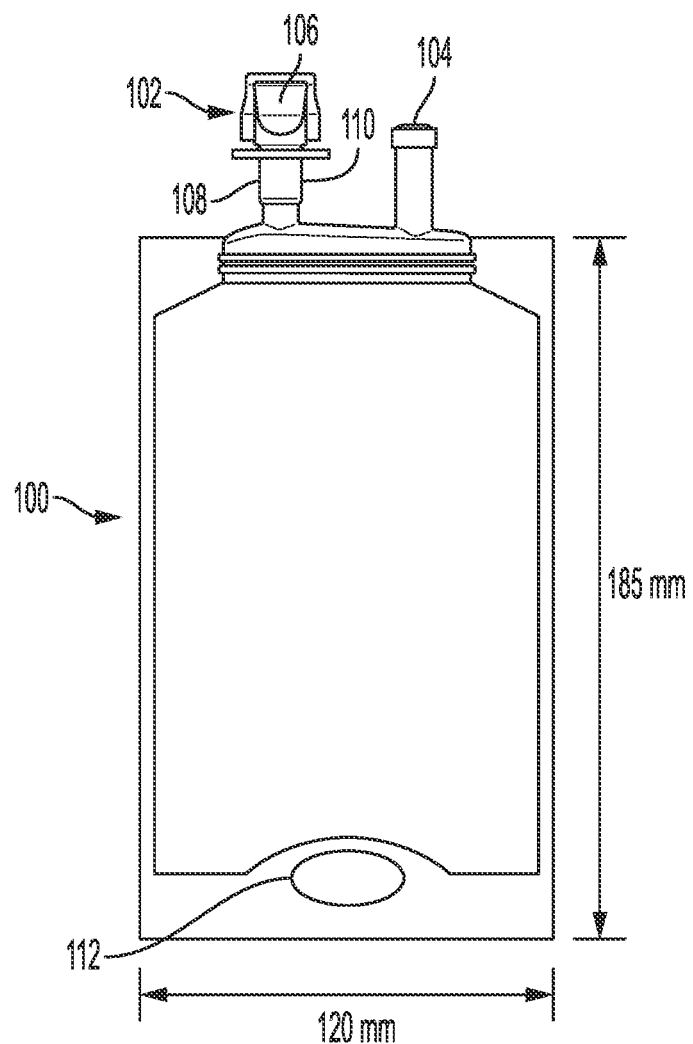
FIG. 2A is a plan view of an exemplary secondary container according to the disclosure.
Figure 2B:
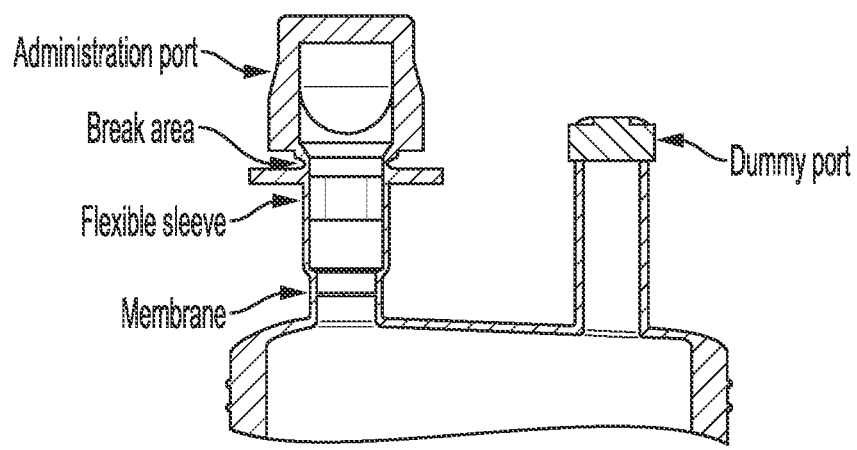
FIG. 2B is a diagram of an exemplary port system including an administration port and a non-accessible (dummy) port.

FIGS. 2A, 2B illustrate a suitable primary container 100 according to the disclosure. As illustrated, the primary container is a plastic bag with a single functioning port 102. The single port 102 is an administration port for delivering the formulation of an oxygen-sensitive pharmaceutical compound such as the ready-to-use, stable norepinephrine formulation disclosed herein to a patient. The primary container 100 further includes a non-accessible "dummy" port 104. A twist-off protective cap 106 is provided to protect the administration port 102. The administration port 102 is fluidly connected to a contents of the primary container 100 via a flexible sleeve 108 defining a channel capable of fluid communication with the contents of the primary container. As illustrated, the channel is not in fluid communication with the contents of the primary container 100 until a membrane 110 is pierced or otherwise opened. The primary container 100 further includes a hanger hole 112. It should be understood that the dimensions provided in FIG. 2A merely illustrative and not limiting.

Figure 3:
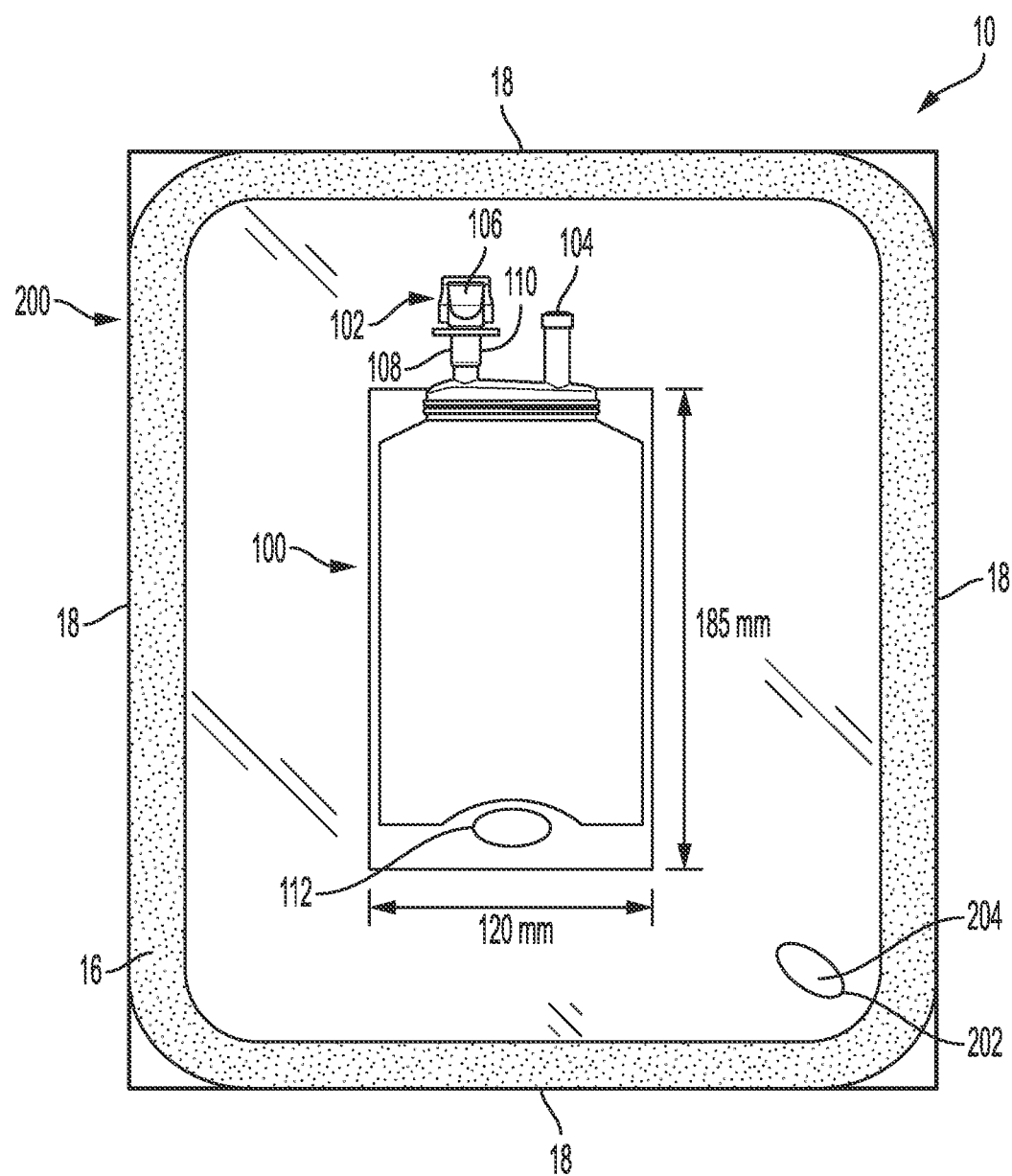
FIG. 3 is a plan view of a primary container and at least one oxygen scavenger disposed within the secondary container of FIG. 2A.

FIG. 3 illustrates a representative packaged, sealed container system 200 according to the disclosure. The packaged, sealed container system 200 includes the primary container 100 disposed within the secondary container 100. The packaged, sealed container system 200 further includes a sachet 202 disposed within the secondary container 100. An oxygen scavenger 204 is contained within the sachet 202 and is in fluid communication with a contents of the primary container 100.

Hereinafter, the packaged, sealed container system and norepinephrine formulations according to the disclosure will be more specifically described by way of examples. The examples are not intended to limit the scope of the invention and are merely used as illustrations.

EXAMPLES

Example 1—Exploration of Parameters

Formulation parameters, such as antioxidant concentration and solution pH, were evaluated. Lab-scale batches were prepared and filled into containers through cut corners (resealed). Containers were subsequently vacuum sealed into overpouches. All formulations were prepared in 0.9% sodium chloride. Oxygen levels were controlled by preparing samples within a glove box under $N_2$ atmosphere. Replicates were tested pre and post sterilization. Runs were evaluated by $O_2$ content (head space and solution), pH, concentration of analyte and related compounds, enantiomeric purity, amount of antioxidant, and "visual inspection."

The following table shows the evaluated formulations:

| Antioxidant | Antioxidant amount (mg/mL) | Formulation pH |
|---|---|---|
| None | 0.0 | 2.5 |
|  | 0.0 | 2.5 |
|  | 0.0 | 2.5 |
|  | 0.0 | 3.5 |
|  | 0.0 | 4.5 |
|  | 0.0 | 4.5 |
| Metabisulfite (SMB) | 0.3 | 4.0 |
|  | 0.5 | 3.5 |
|  | 0.5 | 3.5 |
|  | 0.8 | 3.0 |
|  | 1.0 | 2.5 |
|  | 1.0 | 4.5 |
|  | 1.0 | 4.5 |
| Cysteine (CYS) | 0.5 | 2.5 |
|  | 0.5 | 3.5 |
|  | 0.5 | 3.5 |
|  | 0.8 | 4.0 |
|  | 1.0 | 2.5 |
|  | 1.0 | 4.5 |

Figure 4:
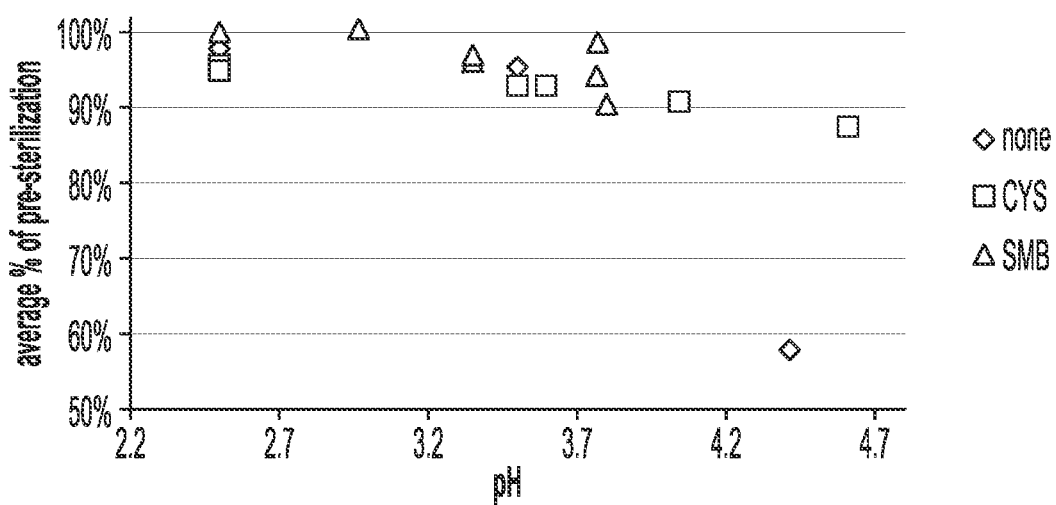
FIG. 4 is a graph illustrating the effect of pH on norepinephrine concentration in 0.9% sodium chloride after terminal sterilization by autoclaving.
Figure 5:
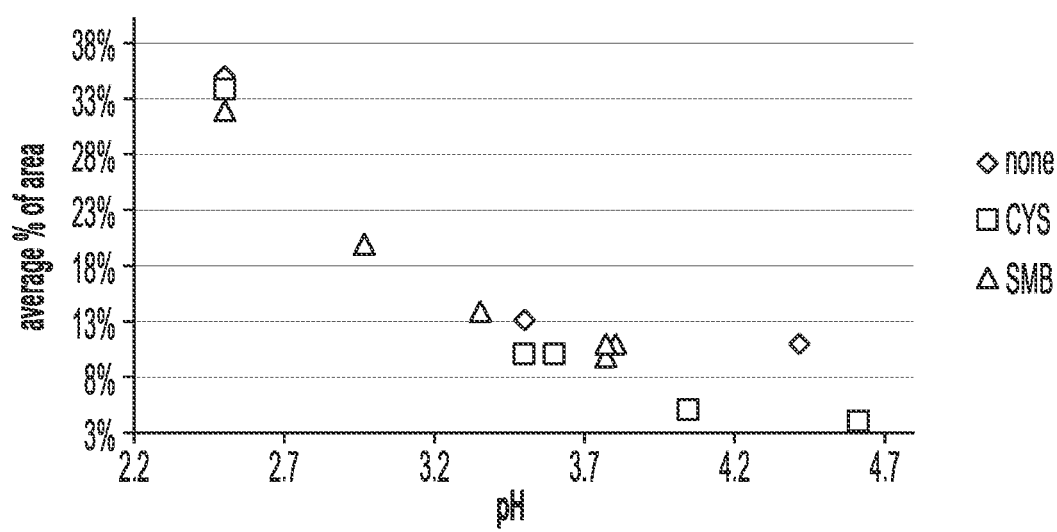
FIG. 5 is a graph illustrating the effect of pH on the concentration of the S-isomer of norepinephrine after terminal sterilization by autoclaving.

Nineteen formulations were prepared in accordance with the table above. FIG. 4 shows the effect of pH on norepinephrine concentration. FIG. 5 shows the effect of pH on the concentration of the S-isomer of norepinephrine. It was determined that higher pH values decreased the rate of epimerization to the S-isomer, whereas lower pH values decreased the rate of norepinephrine oxidation. These data show that an antioxidant-free and ready-to-use norepinephrine formulation according to the invention is as stable toward oxidation and epimerization as one containing metabisulfite as an antioxidant (see, e.g., FIGS. 4 and 5, pH 3.5), and is surprisingly more stable than a formulation with cysteine. Moreover, the formulation was surprisingly stable as formulated in saline.

Example 2—Long-Term Stability Studies

Sterilization process: The solution was sparged with $N_2$. The primary head space was minimized to ~ 5 mL, and annular head space was minimized to ~ 10 mL, but no attempt was made to deoxygenate either head space.

"Intense" sterilization process: The solution was sparged with $N_2$. $N_2$ was introduced into the primary head space of the primary container (~20 mL) through the administration port; and $N_2$ was introduced into head space of the secondary container (~ 100 mL) to effect further deoxygenation.

The following formulations were tested in 5% dextrose for long-term stability:

| Formulation | Norepinephrine Dose (mg/L) | Antioxidant | pH |
| --- | --- | --- | --- |
| 1A | 16 | Sodium metabisulfite | 3.2-4.7 |
| 1B | 32 | Sodium metabisulfite | 4.2 |
| 2 | 16 | none | 3.2-4.3 |

Figure 6:
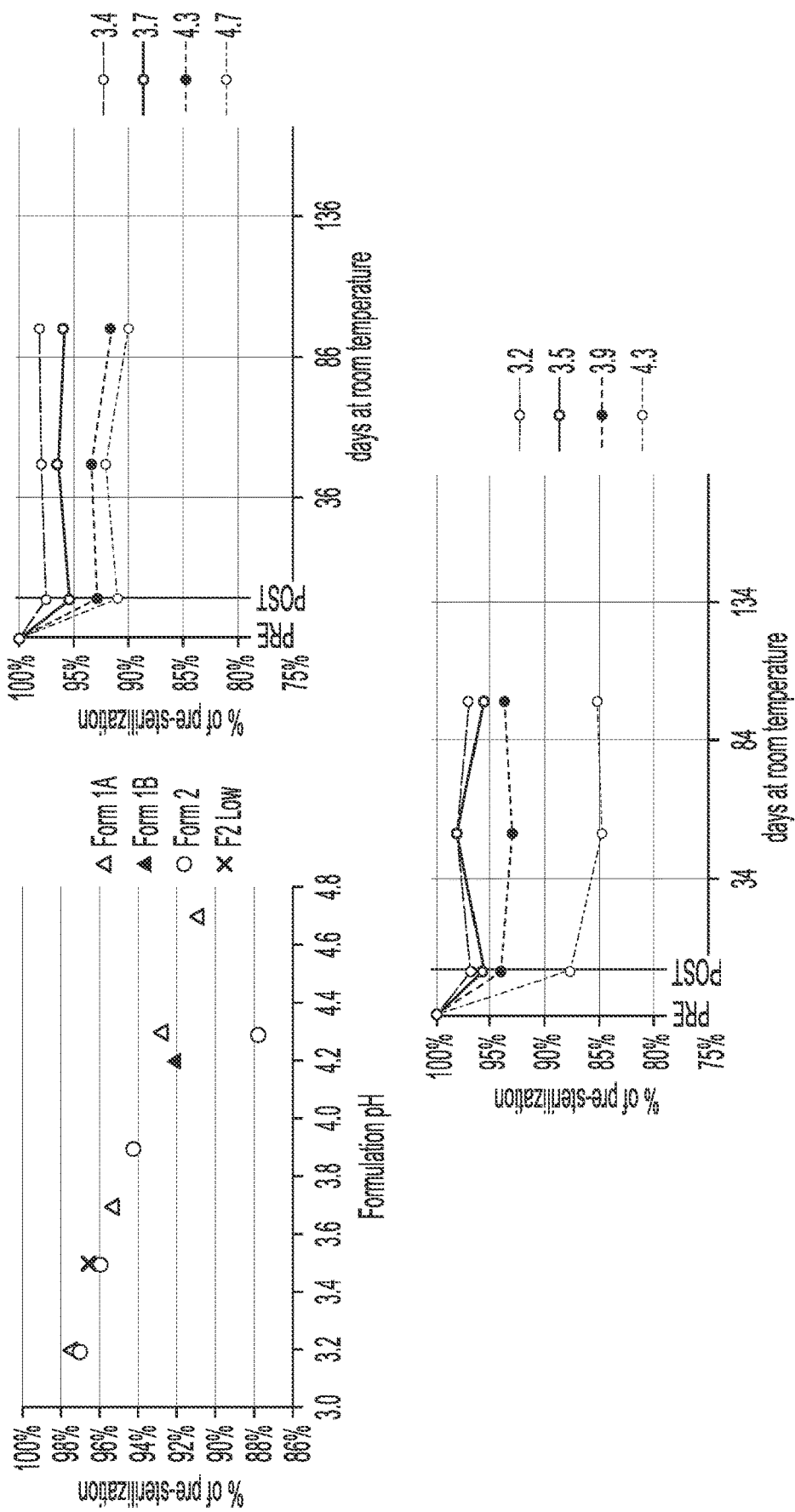
FIG. 6 illustrates the change in norepinephrine concentration in formulations with antioxidant and without antioxidant in response to pH and time.
Figure 7:
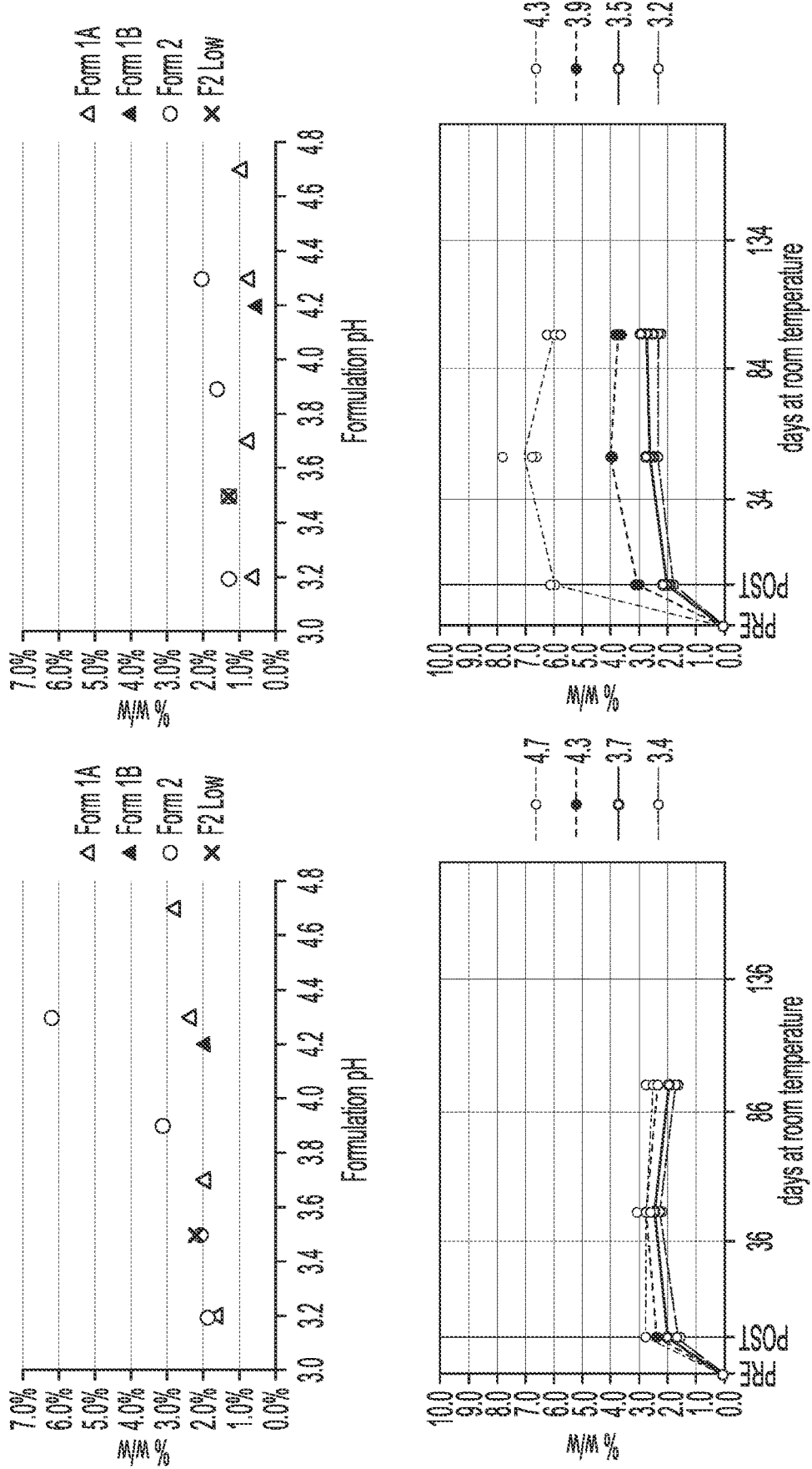
FIG. 7 illustrates the change in the total concentration of norepinephrine degradation products in formulations with antioxidant and without antioxidant in response to pH and time.
Figure 8:
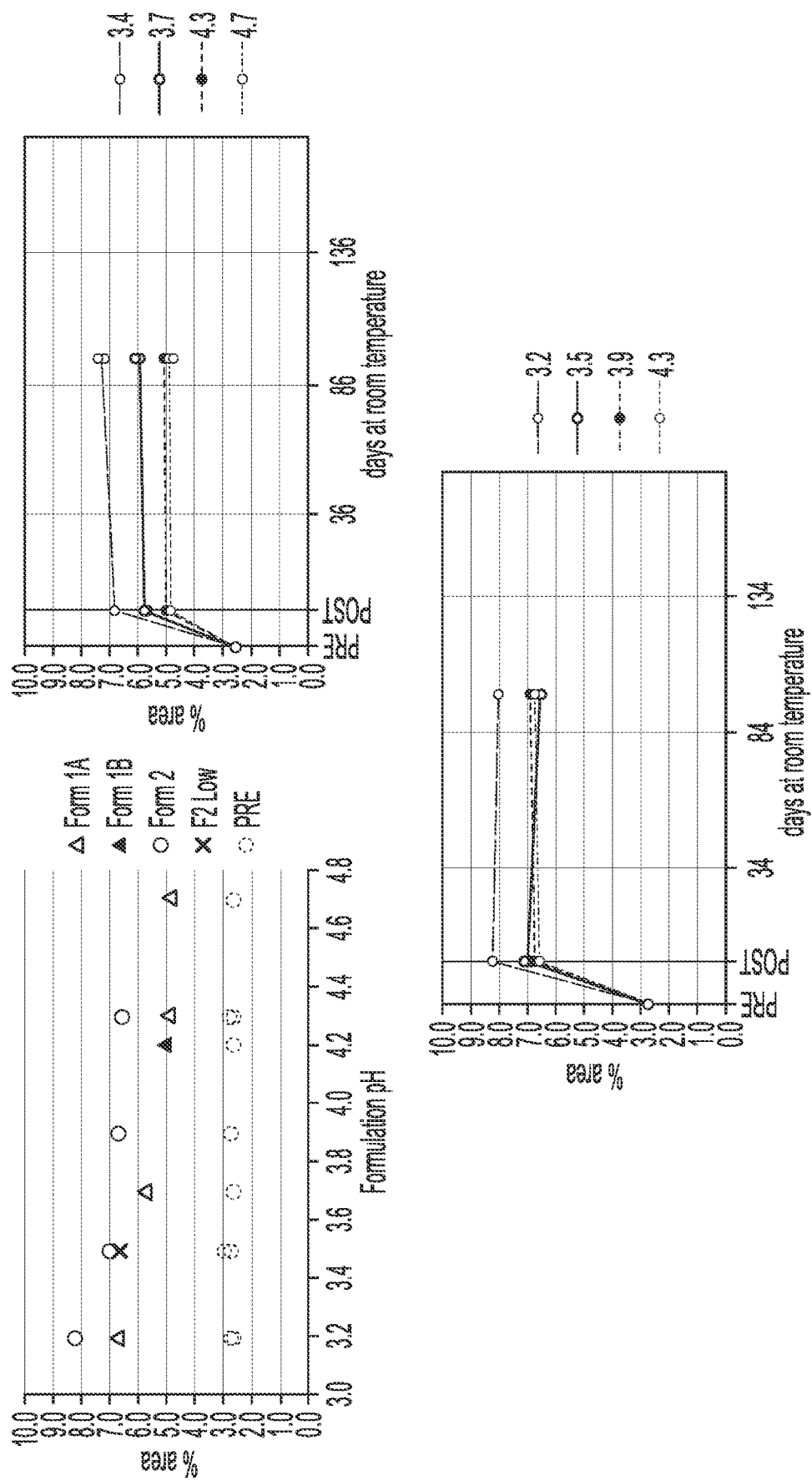
FIG. 8 illustrates the change in the concentration of the S-isomer of norepinephrine in formulations with antioxidant and without antioxidant in response to pH and time.
Figure 9:
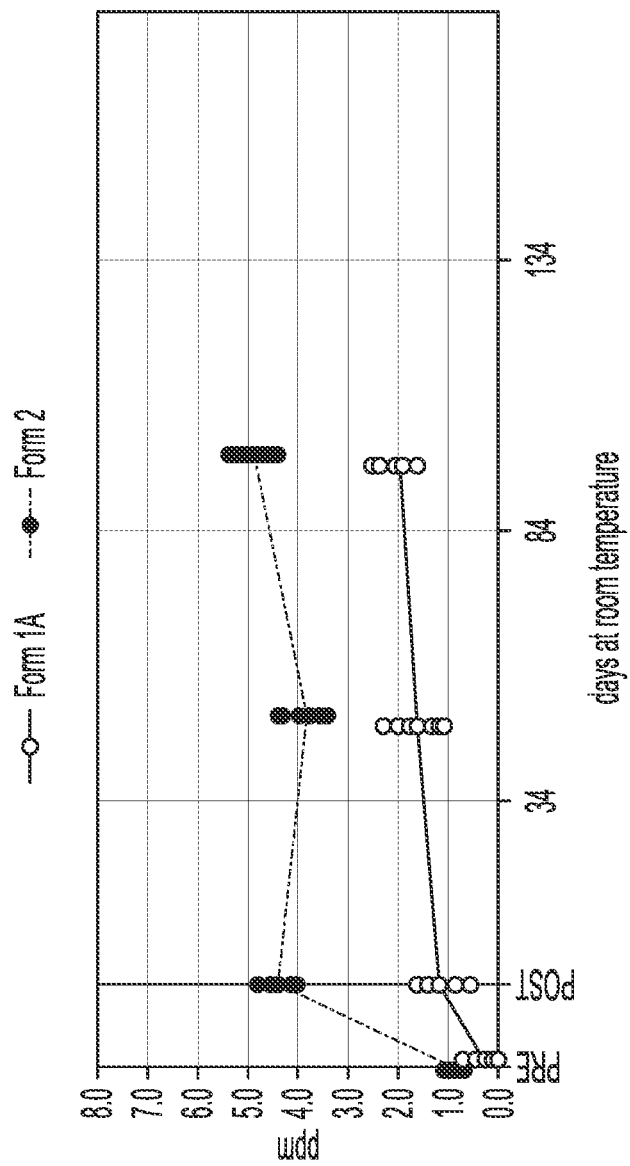
FIG. 9 is a graph illustrating the change in the concentrations of dissolved oxygen in formulations with antioxidant and without antioxidant over time.
Figure 10:
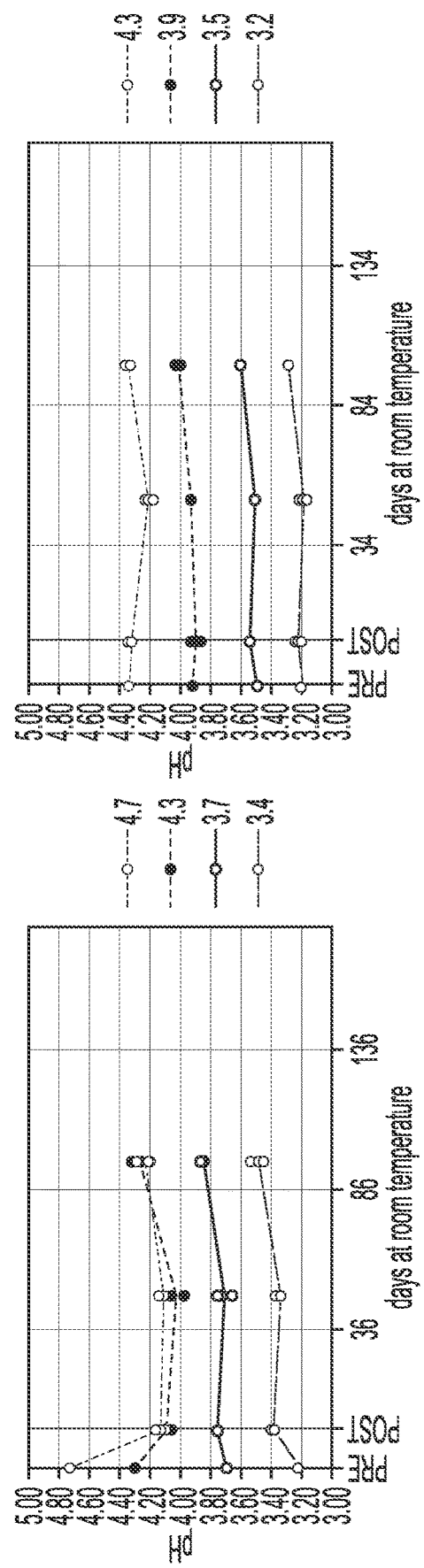
FIG. 10 illustrates the change in pH of norepinephrine formulations with antioxidant and without antioxidant over time.

FIG. 6 shows the change in norepinephrine concentration of these formulations in response to pH and over time. FIG. 7 shows the change in the total concentration of degradation products of norepinephrine in these formulations in response to pH and over time. FIG. 8 shows the change in the concentration of the S-isomer of norepinephrine in these formulations in response to pH and over time. FIG. 9 shows the change in the concentrations of oxygen in these formulations over time. FIG. 10 shows the change in pH of these formulations over time. "F2 Low" corresponds to Formulation 2 after undergoing intense sterilization. These data further show that the performance of an antioxidant-free formulation compares favorably with that of a formulation containing a metabisulfite antioxidant, especially at pH values lower than 4.2.

Example 3—Effect of Packaged, Sealed Container System with Oxygen Scavenger

Norepinephrine formulations according to the disclosure were sparged with nitrogen during manufacturing to drive the dissolved oxygen down as far as possible as generally described above. As shown in FIG. 11, in both cases, dissolved oxygen content was initially below 0.5 ppm. In both cases, the primary and secondary containers were the same. The secondary overpouch container allows oxygen to pass into the annular space between the primary container and the secondary overpouch container. The oxygen will equilibrate with the head space in the primary container over the solution. The oxygen in the head space above the solution will then dissolve into the aqueous solution to form an equilibrium between dissolved oxygen and the head space oxygen according to Henry's Law.

Dissolved oxygen is what causes degradation of an oxygen sensitive pharmaceutical compound, such as norepinephrine. In the original formulation, the dissolved oxygen increased from ~0.5 ppm to ~2.8 ppm over two years. This allowed oxidation of the pharmaceutical to occur and accelerate over time. The formulation with the oxygen scavenger surprisingly reduced the dissolved oxygen down to about 0 ppm by scavenging (e.g., reacting with) the oxygen in the annular space of the secondary container. As the oxygen in the annular space was decreased, the head space in the primary container equilibrated with the low oxygen annular space to decrease the oxygen content in the head space of the primary container. The dissolved oxygen in the solution equilibrated with the oxygen content in the head space of the primary container per Henry's Law causing the dissolved oxygen levels to drop to ~0 ppm.

What is claimed:

1. A packaged, sealed container system for stable storage of a ready-to-use, stable norepinephrine formulation, the packaged, sealed container system comprising:
    a primary container comprising a ready-to-use, stable norepinephrine formulation therein, the ready-to-use, stable norepinephrine formulation comprising:
    0.015 mg/ml to about 0.035 mg/ml norepinephrine;
    dextrose; and
    a pH between 3.4 and 4.0;
    wherein the ready-to-use, stable norepinephrine formulation is free of an antioxidant;
    a secondary container comprising a first flexible sheet comprising a coextruded film including a metal foil, an opposing second flexible sheet layer which is colored to protect the ready-to-use, stable norepinephrine formulation from light, and a seal disposed along a common peripheral edge of the first and second flexible sheet layers, wherein the primary container is disposed between and enclosed by the first and second flexible sheet layers of the secondary container; and
    an oxygen scavenger disposed between and enclosed by the first and second flexible sheet layers of the secondary container, the oxygen scavenger being in fluid communication with the contents of the primary container,
    wherein the primary container is a multi-layer bag comprising a third flexible sheet layer of low-density polyethylene, an opposing fourth flexible sheet layer of polypropylene, a middle polyamide layer, and a primary container seal disposed along a common peripheral edge of the third and fourth flexible sheet layers; and
    wherein the ready-to-use, stable norepinephrine formulation does not comprise sodium chloride,
    wherein the norepinephrine is in the form of norepinephrine bitartrate monohydrate,
    wherein the ready-to-use, stable norepinephrine formulation has a dissolved oxygen level of less than 0.5 ppm after storage for at least 150 days at 25° C., and
    wherein the ready-to-use, stable norepinephrine formulation retains at least about 90% of an initial activity as measured by an initial and a final amount of R-norepinephrine present in the formulation after storage for at least 120 days at 25° C.

2. The packaged, sealed container system for stable storage of a ready-to-use, stable norepinephrine formulation according to claim 1, wherein the primary container has a single port, the single port comprising an administration port for delivering the ready-to-use, stable norepinephrine formulation to a patient.

3. The packaged, sealed container system for stable storage of a ready-to-use, stable norepinephrine formulation according to claim 1, wherein the third or the fourth flexible sheets are coextruded film laminates comprising a polypropylene layer.

4. The packaged, sealed container system for stable storage of a ready-to-use, stable norepinephrine formulation according to claim 3, wherein the coextruded film laminates further comprise a polyamide layer.

5. The packaged, sealed container system for stable storage of a ready-to-use, stable norepinephrine formulation according to claim 1, wherein the metal foil of the coextruded film is an aluminum foil.

6. The packaged, sealed container system for stable storage of a ready-to-use, stable norepinephrine formulation according to claim 1, wherein the opposing second flexible sheet layer comprises a transparent coextruded film configured to allow visual inspection into the secondary container.

7. The packaged, sealed container system for stable storage of a ready-to-use, stable norepinephrine formulation according to claim 1, wherein the opposing second flexible sheet layer is amber colored.

8. The packaged, sealed container system for stable storage of a ready-to-use, stable norepinephrine formulation according to claim 1, wherein the second flexible sheet layer has a water transmission rate less than 3.0 g/m$^2$/day.

9. The packaged, sealed container system for stable storage of a ready-to-use, stable norepinephrine formulation according to claim 1, wherein the oxygen scavenger comprises iron powder, iron oxide powder, or a mixture thereof.

10. The packaged, sealed container system for stable storage of a ready-to-use, stable norepinephrine formulation according to claim 1, wherein the concentration of norepinephrine is between about 0.015 mg/ml and about 0.020 mg/ml.

11. The packaged, sealed container system for stable storage of a ready-to-use, stable norepinephrine formulation according to claim 1, wherein the concentration of norepinephrine is between about 0.030 mg/ml and about 0.035 mg/ml.

12. The packaged, sealed container system for stable storage of a ready-to-use, stable norepinephrine formulation according to claim 1, wherein the pH is between about 3.5 and about 3.9.

13. The packaged, sealed container system for stable storage of a ready-to-use, stable norepinephrine formulation according to claim 1, wherein the pH is between about 3.6 and about 3.8.

14. A method of treating hypotension in a subject, the method comprising:
    opening the packaged, sealed container system for stable storage of a ready-to-use, stable norepinephrine formulation according to claim 1; and
    administering to a subject a therapeutically effective amount of the ready-to-use, stable norepinephrine formulation,
    wherein the subject is in need of treatment for hypotension.

15. The method of claim 14 wherein the subject has a condition selected from one or more of pheochromocytomectomy, sympathectomy, poliomyelitis, spinal anesthesia, myocardial infarction, septicemia, blood transfusion, and drug reactions.

16. The method of claim 14 wherein the subject has a condition selected from one or more of cardiac arrest and profound hypotension.

17. The packaged, sealed container system according to claim 1, wherein the ready-to-use, stable norepinephrine formulation has a dissolved oxygen level of less than 0.1 ppm after storage for at least 150 days at 25° C.

18. The packaged, sealed container system according to claim 1, wherein the ready-to-use, stable norepinephrine formulation has a dissolved oxygen level of less than 0.5 ppm after storage for at least 180 days at 25° C.

19. The packaged, sealed container system according to claim 1, wherein the ready-to-use, stable norepinephrine formulation has a dissolved oxygen level of less than 0.1 ppm after storage for at least 180 days at 25° C.

20. A packaged, sealed container system for stable storage of a ready-to-use, stable norepinephrine formulation, the packaged, sealed container system comprising:
    a primary container comprising a ready-to-use, stable norepinephrine formulation therein, wherein the primary container is a multi-layer bag comprising a third flexible sheet layer of low-density polyethylene, an opposing fourth flexible sheet layer of polypropylene, a middle polyamide layer, and a primary container seal disposed along a common peripheral edge of the third and fourth flexible sheet layers;
    a secondary container comprising a first flexible sheet layer comprising a coextruded film including a metal foil, an opposing second flexible sheet layer which is colored to protect the ready-to-use, stable norepinephrine formulation from light, and a seal disposed along a common peripheral edge of the first and second flexible sheet layers, wherein the primary container is disposed between and enclosed by the first and second flexible sheet layers of the secondary container; and
    an oxygen scavenger disposed between and enclosed by the first and second flexible sheet layers of the secondary container, the oxygen scavenger being in fluid communication with the contents of the primary container,
    wherein the ready-to-use, stable norepinephrine formulation consists essentially of 0.015 mg/ml to about 0.035 mg/ml norepinephrine;
    dextrose;
    water; and
    optionally, hydrochloric acid and/or sodium hydroxide as pH adjusters,
    wherein the ready-to-use, stable norepinephrine formulation has a pH between 3.4 and 4.0, and has a dissolved oxygen level of less than 0.5 ppm after storage for at least 150 days at 25° C.,
    wherein the ready-to-use, stable norepinephrine formulation retains at least about 90% of an initial activity as measured by an initial and a final amount of R-norepinephrine present in the formulation after storage for at least 120 days at 25° C., and
    wherein the norepinephrine is in the form of norepinephrine bitartrate monohydrate.

21. The packaged, sealed container system according to claim 20, wherein the norepinephrine is present at a concentration of 0.015 mg/ml to 0.020 mg/ml or 0.030 to 0.035 mg/ml.

22. The packaged, sealed container system according to claim 20, wherein the ready-to-use, stable norepinephrine formulation has a dissolved oxygen level of less than 0.1 ppm after storage for at least 150 days at 25° C.

23. The packaged, sealed container system according to claim 20, wherein the ready-to-use, stable norepinephrine formulation has a dissolved oxygen level of less than 0.5 ppm or less than 0.1 ppm after storage for at least 180 days at 25° C.

24. A packaged, sealed container system comprising:
a ready-to-use, stable norepinephrine formulation consisting of 0.015 mg/ml to 0.035 mg/ml norepinephrine and dextrose, wherein the ready-to-use, stable norepinephrine formulation has a pH of 3.4-4.0 and has a dissolved oxygen level of less than 0.5 ppm after storage for at least 150 days at 25° C., wherein the ready-to-use, stable norepinephrine formulation retains at least about 90% of an initial activity as measured by an initial and a final amount of R-norepinephrine present in the formulation after storage for at least 120 days at 25° C., and wherein the norepinephrine is in the form of norepinephrine bitartrate monohydrate;
a primary container comprising the ready-to-use, stable norepinephrine formulation therein, wherein the primary container is a multilayer bag comprising third flexible sheet layer of low-density polyethylene, an opposing fourth flexible sheet of polypropylene, a polyamide middle layer, and a primary container seal disposed along a common peripheral edge of the third and fourth flexible sheet layers;
a secondary container comprising a first flexible sheet layer comprising a coextruded film including a metal foil, an opposing second flexible sheet layer which is colored to protect the ready-to-use, stable norepinephrine formulation from light, and a seal disposed along a common peripheral edge of the first and second flexible sheet layers, wherein the primary container is disposed between and enclosed by the first and second flexible sheet layers of the secondary container; and
an oxygen scavenger disposed between and enclosed by the first and second flexible sheet layers of the secondary container, the oxygen scavenger being in fluid communication with the contents of the primary container.

25. The packaged, sealed container system according to claim 24, wherein the ready-to-use, stable norepinephrine formulation has a dissolved oxygen level of less than 0.1 ppm after storage for at least 150 days at 25° C.

26. The packaged, sealed container system according to claim 24, wherein the ready-to-use, stable norepinephrine formulation has a dissolved oxygen level of less than 0.5 ppm or less than 0.1 ppm after storage for at least 180 days at 25° C.

27. A packaged, sealed container system comprising:
a ready-to-use, stable norepinephrine formulation consisting of 0.015 mg/ml to 0.035 mg/ml norepinephrine, dextrose, and hydrochloric acid and/or sodium hydroxide as pH adjusters, wherein the ready-to-use, stable norepinephrine formulation has a pH of 3.4-4.0 and has a dissolved oxygen level of less than 0.5 ppm after storage for at least 150 days at 25° C., and wherein the norepinephrine is in the form of norepinephrine bitartrate monohydrate, and wherein the ready-to-use, stable norepinephrine formulation retains at least about 90% of an initial activity as measured by an initial and a final amount of R-norepinephrine present in the formulation after storage for at least 120 days at 25° C.;
a primary container comprising the ready-to-use, stable norepinephrine formulation therein, wherein the primary container is a multi-layer bag comprising a third flexible sheet layer of low-density polyethylene, an opposing fourth flexible sheet layer of polypropylene, a middle polyamide layer, and a primary container seal disposed along a common peripheral edge of the third and fourth flexible sheet layers;
a secondary container comprising a first flexible sheet layer comprising a coextruded film including a metal foil, an opposing second flexible sheet layer which is colored to protect the ready-to-use, stable norepinephrine formulation from light, and a seal disposed along a common peripheral edge of the first and second flexible sheet layers, wherein the primary container is disposed between and enclosed by the first and second flexible sheet layers of the secondary container; and
an oxygen scavenger disposed between and enclosed by the first and second flexible sheet layers of the secondary container, the oxygen scavenger being in fluid communication with the contents of the primary container.

28. The packaged, sealed container system according to claim 27, wherein the ready-to-use, stable norepinephrine formulation has a dissolved oxygen level of less than 0.1 ppm after storage for at least 150 days at 25° C.

29. The packaged, sealed container system according to claim 27, wherein the ready-to-use, stable norepinephrine formulation has a dissolved oxygen level of less than 0.5 ppm or less than 0.1 ppm after storage for at least 180 days at 25° C.

30. The packaged, sealed container system according to claim 27, wherein the formulation consists of 0.015 mg/ml to 0.020 mg/ml or 0.030 to 0.035 mg/ml norepinephrine.

* * * * *